United States Patent [19]

Matsumoto

[11] Patent Number: 5,668,083
[45] Date of Patent: Sep. 16, 1997

[54] COMPOSITION CONTAINING 3-ISOTHIAZOLONE AND STABILIZER

[75] Inventor: Masahiro Matsumoto, Urawa, Japan

[73] Assignee: Rohm and Haas Company, Philadelphia, Pa.

[21] Appl. No.: 683,296

[22] Filed: Jul. 18, 1996

Related U.S. Application Data

[63] Continuation of Ser. No. 469,973, Jun. 6, 1995, abandoned.

[51] Int. Cl.$^6$ ..................................... A01N 43/80
[52] U.S. Cl. ..................... 504/138; 504/156; 514/244; 514/439; 514/445
[58] Field of Search .................... 504/138, 156; 514/244, 439, 445

[56] References Cited

U.S. PATENT DOCUMENTS

| | | | |
|---|---|---|---|
| 3,870,795 | 3/1975 | Miller et al. | 424/270 |
| 4,067,878 | 1/1978 | Miller et al. | 260/302 |
| 4,824,957 | 4/1989 | Amick | 548/213 |
| 4,906,274 | 3/1990 | Mattox | 71/67 |
| 4,906,651 | 3/1990 | Hsu | 514/372 |
| 4,964,892 | 10/1990 | Hsu | 71/67 |
| 5,142,058 | 8/1992 | Willingham et al. | 548/213 |
| 5,242,893 | 9/1993 | Willingham | 504/138 |
| 5,292,763 | 3/1994 | Hsu et al. | 514/372 |

FOREIGN PATENT DOCUMENTS

| | | |
|---|---|---|
| 166611 | 11/1985 | European Pat. Off. . |
| 398795 | 5/1990 | European Pat. Off. . |
| 503175 | 3/1991 | European Pat. Off. . |

*Primary Examiner*—Allen J. Robinson
*Assistant Examiner*—Brian G. Bembenick
*Attorney, Agent, or Firm*—Julie J. L. Cheng

[57] ABSTRACT

3-Isothiazolone compositions which are stable, free from turbidity, and do not corrode metal storage containers are disclosed. These compositions further have no possibility of coagulating latex or generating nitrosamine.

8 Claims, No Drawings

COMPOSITION CONTAINING 3-ISOTHIAZOLONE AND STABILIZER

This is a continuation of application Ser. No. 08/469,973, filed Jun. 6, 1995 abandoned.

This invention relates to the stabilization of a 3-isothiazolone biocide preparation free of metal salt, and particularly to the stabilization of a mixed preparation of 5-chloro-2-methyl-4-isothiazolin-3-one ("CMI" or 5-chloro-2-methyl-3-isothiazolone) and 2-methyl-4-isothiazolin-3-one ("MI" or 2-methyl-3-isothiazolone), and more particularly aims to stabilize a 3-isothiazolone preparation by adding hexamethylenetetramine ("HMT") and 5-bromo-5-nitro-1,3-dioxane to the 3-isothiazolone.

3-Isothiazolone have been extensively used mainly as a bactericide, mildewcide or algaecide against microorganisms for industrial aqueous and non-aqueous products. When substituted with an appropriate functional group, 3-isothiazolones are very effective biocides and are widely used.

"Biocide" is used herein to include bactericide, germicide, slime control agent and algaecide, and has microbicidal and microbistatic effects.

It has been pointed out that the activity of 3-isothiazolone preparations is lowered during storage or when it is added to a substrate to be treated. This is because the 3-isothiazolone is not stable enough to be stored for a long time under typical storage conditions. Therefore, a process for improving the stability of 3-isothiazolone has been sought. Preparations which have been made commercially available include (1) a preparation prepared by adding water as a solvent to a mixture of CMI and MI with metal nitrate as a stabilizer (U.S. Pat. No. 3,870,795 and U.S. Pat. No. 4,067,878), (2) a preparation prepared by adding glycol as a solvent and orthoesters as a stabilizer (U.S. Pat. No. 4,906,274), (3) a preparation prepared by adding glycol as a solvent but not including a stabilizer, and (4) a preparation prepared by adding glycol and/or water as a solvent and a certain type of nitrobromo compound as a stabilizer. In recent years, a preparation using glycol or water as a solvent and HMT as a stabilizer has been proposed (U.S. Pat. No. 5,242,893).

When the 3-isothiazolone preparation of (1), (2) or (3) described above is used in a polymer emulsion or paint or aqueous adhesive using the polymer emulsion as a substrate, there have been unfavorable phenomena such as coagulation of the latex and phase separation. The causes of such phenomena are considered to be the metal nitrate salt or organic solvent that locally contacts with the emulsion at a high concentration or is insoluble in a non aqueous medium. Metal nitrate salts have a further drawback in that they can form a carcinogen, nitrosamine, in 3-isothiazolone compositions containing nitrosamine precursors. Some of the prior art compositions are corrosive to steel.

Therefore, isothiazolone preparations have been demanded which can be stored for a long period, as described above, without forming turbidity or precipitate and which are non-corrosive to steel. This invention has solved these technical problems by combining several types of stabilizers without using magnesium nitrate. This invention also provides a composition which is non-corrosive to metal storage containers.

This invention comprises a composition comprising:

(a) at least one 3-isothiazolone biocide having the general formula (I):

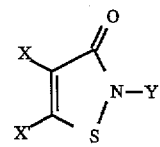

wherein X and X' rare independently selected from the group consisting of hydrogen or halogen; Y is hydrogen or an alkyl group;

(b) hexamethylenetetramine;

(c) 5-bromo-5-nitro-1,3-dioxane; and (d) solvent selected from the group of a water miscible organic solvent and a mixture of water and said water miscible organic solvent.

The 3-isothiazolone in the compositions of this invention is stable for a long period, and does not form a precipitate. Therefore, the industrial biocide aqueous composition of this invention can be used in the same way as conventional biocides and preferably used for polymeric emulsion, paint, adhesive, pigment, treating solution for printing matrix, cooling water, white water in paper making process, and cosmetics, and more preferably used for synthetic polymer emulsion, water-based paint, cutting lubricant and others. For example, when the aqueous composition of this invention is used as a biocide for polymer emulsion, it is desirable that the emulsion does not gel and that metal storage containers are not corroded.

Suitable 3-isothiazolones include, for example, 5-chloro-2-methyl-4-isothiazolin-3-one, 2-methyl-4-isothiazolin-3-one, 4-chloro-2-methyl-4-isothiazolin-3-one, 4,5-dichloro-2-methyl-4-isothiazolin-3-one, 5-bromo-2-methyl-4-isothiazolin-3-one, or mixtures thereof. A mixture of 5-chloro-2-methyl-4-isothiazolin-3-one and 2-methyl-4-isothiazolin-3-one at a ratio of from 3:1 to 10:1 is preferred. Such 3-isothiazolone compounds are preferably present in 10% or less in the composition.

Then, HMT (b) is added to the composition of the 3-isothiazolone compound (a) as a stabilizer. The HMT in the composition is from 0.01 to 1.0% by weight, and preferably from 0.05 to 0.5% by weight of the composition of the invention.

5-Bromo-5-nitro-1,3-dioxane, which is added as a third component (c), is also broadly used as an industrial biocide. 5-Bromo-5-nitro-1,3-dioxane in the composition is from 0.1 to 1.0% by weight, and preferably from 0.4 to 1.0% by weight of the composition of the invention.

For the compositions of this invention, a water miscible organic solvent or a mixture of water and said water miscible organic solvent sufficient to dissolve the above components (a), (b) and (c) are used. Suitable water miscible organic solvents are glycol-based solvents. Ethylene glycol, dipropylene glycol and diethylene glycol are preferred. They have been broadly used as solvents for 3-isothiazolone based compounds.

The compositions of this invention are formed by adding the other components of this invention to a preparation which contains the 3-isothiazolone. For example, to a 3-isothiazolone preparation containing glycol-based solvent, the remaining components may be added; or to this 3-isothiazolone preparation, HMT or 5-bromo-5-nitro-1,3-dioxane may be added successively to produce the composition. Obviously, these components (a) through (c) may be added simultaneously.

Examples of this invention will be described below. It is to be understood that these examples do not restrict the present invention except for being restricted by the claims.

Unless otherwise specified, all percentages are by weight, and the reagents are of commercially available grade.

EXAMPLE 1

A mixture consisting of CMI and MI in a ratio of 3:1 (a product of Rohm and Haas, USA) was dissolved in dipropylene glycol to prepare a solution having a concentration of 25%. To this solution, 5-bromo-5-nitro-1,3-dioxane, hexamethylenetetramine (made by Kanto Chemical Co., Ltd.) and water were added to prepare the following test solutions as shown in Table I.

TABLE I

| Test solution | % 3-Isothiazolone | % 5-Bromo-5-nitro-1,3-dioxane | % HMT |
|---|---|---|---|
| 1-1# | 6.63 | 0.8 | — |
| 1-2# | 6.63 | — | 1.0 |
| 1-3 | 6.63 | 0.2 | 0.05 |
| 1-4 | 6.63 | 0.2 | 0.1 |
| 1-5 | 6.63 | 0.2 | 0.5 |
| 1-6 | 6.63 | 0.2 | 1.0 |
| 1-7 | 6.63 | 0.4 | 0.05 |
| 1-8 | 6.63 | 0.4 | 0.1 |
| 1-9 | 6.63 | 0.4 | 0.5 |
| 1-10 | 6.63 | 0.4 | 1.0 |
| 1-11 | 6.63 | 0.4 | 1.2 |
| 1-12 | 6.63 | 0.6 | 0.05 |
| 1-13 | 6.63 | 0.6 | 0.1 |
| 1-14 | 6.63 | 0.6 | 0.5 |
| 1-15 | 6.63 | 0.6 | 1.0 |
| 1-16 | 6.63 | 0.6 | 1.2 |

# = Comparative

The test solutions were stored at 40° C. for 4 weeks. The solutions analyzed for % CMI remaining, turbidity, and precipitate formation. The results are shown in Tables II and III.

TABLE II

% CMI Remaining After Storage at 40° C.

| Test Solution | 1 Week | 2 Weeks | 3 Weeks | 4 Weeks |
|---|---|---|---|---|
| 1-1# | 100 | 99.8 | 98.6 | 97.2 |
| 1-2# | 97.0 | 89.0 | 71.9 | 64.4 |
| 1-3 | 100 | 99.4 | 98.6 | 98.5 |
| 1-4 | 100 | 99.8 | 98.6 | 98.4 |
| 1-5 | 100 | 99.6 | 99.4 | 99.2 |
| 1-6 | 100 | 99.7 | 99.5 | 99.1 |
| 1-7 | 100 | 99.4 | 99.3 | 99.1 |
| 1-8 | 100 | 98.6 | 98.0 | 97.6 |
| 1-9 | 100 | 99.5 | 97.8 | 97.5 |
| 1-10 | 100 | 97.4 | 97.2 | 95.8 |
| 1-11 | 100 | 99.4 | 96.9 | 96.5 |
| 1-12 | 100 | 98.4 | 96.6 | 96.3 |
| 1-13 | 100 | 99.4 | 98.8 | 98.0 |
| 1-14 | 100 | 99.0 | 98.0 | 98.0 |
| 1-15 | 100 | 99.7 | 98.0 | 98.6 |
| 1-16 | 100 | 99.0 | 98.4 | 96.8 |

# = Comparative

TABLE III

Turbidity and Precipitate Formation in Test Solutions After Storage at 40° C.

| Test Solution | 0 Week | 1 Week | 2 Weeks | 3 Weeks | 4 Weeks |
|---|---|---|---|---|---|
| 1-1# | 0 | 0+ | 0+ | 0++ | 0+++ |
| 1-2# | 0 | 0+ | 0+ | 0++ | 2+++ |
| Control* | 0 | 2+ | 2++ | 2+++ | 2+++ |
| 1-3 | 0 | 0+ | 0+ | 0++ | 0++ |
| 1-4 | 0 | 0 | 0 | 0 | 0 |
| 1-5 | 0 | 0 | 0+ | 0++ | 0+ |
| 1-6 | 0 | 0 | 0+ | 0++ | 0+ |
| 1-7 | 0 | 0 | 0 | 0 | 0 |
| 1-8 | 0 | 0 | 0 | 0 | 0+ |
| 1-9 | 0 | 0 | 0 | 0 | 0+ |
| 1-10 | 0 | 0 | 0 | 0 | 0+ |
| 1-11 | 0 | 0 | 0 | 0 | 0++ |
| 1-12 | 0 | 0 | 0 | 0 | 0+ |
| 1-13 | 0 | 0 | 0 | 0 | 0+ |
| 1-14 | 0 | 0 | 0 | 0 | 0+ |
| 1-15 | 0 | 0 | 0 | 0 | 0+ |
| 1-16 | 0 | 0 | 0 | 0 | 0++ |

# = Comparative
*The control contained only 3-isothiazolone diluted with water.

The numerical values describing the test results in the Table III are as follows:

| Turbidity | | Precipitate Formation | |
|---|---|---|---|
| 0 | Completely clear | + | Few precipitate |
| 1 | Slightly turbid | ++ | Some precipitate |
| 2 | Turbid | +++ | Much precipitate |

EXAMPLE 2

The same procedure as described in Example 1 was used to prepare the following seven test solutions as described in Table IV.

TABLE IV

| Test solution | % 3-Isothiazolone | % 5-Bromo-5-nitro 1,3-dioxane | % HMT |
|---|---|---|---|
| 2-1# | 6.63 | 0 | 0 |
| 2-2# | 6.63 | 0.8 | 0 |
| 2-3 | 6.63 | 0.8 | 0.01 |
| 2-4 | 6.63 | 0.8 | 0.05 |
| 2-5 | 6.63 | 0.8 | 0.1 |
| 2-6 | 6.63 | 0.8 | 0.5 |
| 2-7 | 6.63 | 0.8 | 10 |

# = Comparative

Corrosivity of the test solutions was examined by placing coupons of SUS stainless steel in the test solutions. The test solutions were allowed to stand at 40° C. for 4 weeks. After this time, the test solutions were examined for CMI remaining, turbidity and precipitate formation. The results are shown in Table V.

TABLE V

| Test Solution | % CMI Remaining | | | | Corrosion Resistance | | Turbidity and Precipitate Formation | |
|---|---|---|---|---|---|---|---|---|
| | 1 Week | 2 Weeks | 3 Weeks | 4 Weeks | 1 Week | 4 Weeks | 1 Week | 4 Weeks |
| 2-1# | 98 | 86 | 78 | 69 | + | + | 0 | 2+++ |
| 2-2# | 100 | 96 | 96 | 95 | + | + | 0 | 2+++ |
| 2-3 | 100 | 95 | 95 | 94 | − | − | 0 | 0 |
| 2-4 | 100 | 96 | 94 | 94 | − | − | 0 | 0 |
| 2-5 | 96 | 95 | 95 | 95 | − | − | 0 | 0 |
| 2-6 | 100 | 95 | 95 | 95 | − | − | 0 | 0 |
| 2-7 | 100 | 95 | 95 | 95 | − | − | 0 | 0 |

\# = Comparative

The numerical values describing the test results in the Table V are as follows:

| Corrosion Resistance | | Turbidity | | Precipitate Formation | |
|---|---|---|---|---|---|
| + | Corrosion present | 0 | Completely clear | + | Few precipitate |
| − | No corrosion | 1 | Slightly turbid | ++ | Some precipitate |
| | | 2 | Turbid | +++ | Much precipitate |

Test solutions 3, 4, 5, 6 and 7 appeared transparent, free from turbidity and any precipitate formation. Stainless steel coupons in test solutions 1 and 2 showed evidence of corrosion. Stainless steel coupons in test solutions 3, 4, 5, 6 and 7 showed no evidence of corrosion.

As is obvious from the examples, this invention has made it possible to provide a 3-isothiazolone biocide composition which, when diluted with water, retains the activity of effective components for a long period of time and remains free of precipitate formation and is stable. This invention is particularly significant in the sense of supplying a commercial product as a biocide for latex.

What is claimed:

1. Composition comprising:
   (a) at least one 3-isothiazolone biocide having the general formula:

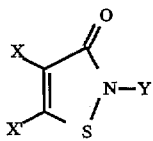

wherein X and X' are independently selected from the group consisting of hydrogen or halogen; and Y is hydrogen or an alkyl group;
   (b) hexamethylenetetramine;
   (c) 5-bromo-5-nitro-1,3-dioxane; and
   (d) solvent selected from the group consisting of a water miscible organic solvent and a mixture of water and said water miscible organic solvent;
   wherein the ingredients (b) and (c) are present in an effective amount so that there is substantially no precipitate formation in said composition upon storage and wherein the composition is non-corrosive to metal storage containers.

2. Composition according to claim 1, wherein said 3-isothiazolone biocide is a mixture of 5-chloro-2-methyl-4-isothiazolin-3-one and 2-methyl-4-isothiazolin-3-one at a ratio of from 3:1 to 10:1.

3. Composition according to claim 1, wherein said hexamethylenetetramine is from 0.01 to 1.0% by weight.

4. Composition according to claim 1, wherein said 5-bromo-5-nitro-1,3-dioxane is from 0.1 to 1:0% by weight.

5. Composition according to claim 1, wherein said water miscible organic solvent is dipropylene glycol.

6. Method of stabilizing a solution of 3-isothiazolone having the general formula

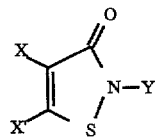

wherein X and X' are independently selected from the group consisting of hydrogen or halogen; and Y is hydrogen or an alkyl group; in a solvent selected from the group consisting of water miscible organic solvent and a mixture of water and said water miscible organic solvent comprising introducing in said solution an effective stabilizing amount of hexamethylenetetramine and 5-bromo-5-nitro-1,3-dioxane wherein the ingredients (b) and (c) are present in an effective amount so that said solution does not form a precipitate upon storage and is non-corrosive to metal storage containers.

7. Composition according to claim 1 wherein there is substantially no precipitate formation in said composition upon storage for 4 weeks at 40° C.

8. Method according to claim 6 wherein wherein said solution wherein said solution does not form a precipitate upon storage for 4 weeks at 40° C.

* * * * *